(12) United States Patent
Ferrer

(10) Patent No.: US 11,395,819 B1
(45) Date of Patent: Jul. 26, 2022

(54) ANTIVIRAL AND VIRUCIDAL LUNG NEBULIZER COMPOSITIONS AND RELATED TREATMENT METHODS

(71) Applicant: FERRER MEDICAL INNOVATIONS, LLC, Aventura, FL (US)

(72) Inventor: Gustavo Ferrer, Southwest Ranches, FL (US)

(73) Assignee: FERRER MEDICAL INNOVATIONS, LLC, Hallandale Beach, FL (US)

( * ) Notice: Subject to any disclaimer, the term of this patent is extended or adjusted under 35 U.S.C. 154(b) by 0 days.

(21) Appl. No.: 17/513,350

(22) Filed: Oct. 28, 2021

Related U.S. Application Data

(63) Continuation of application No. 17/230,321, filed on Apr. 14, 2021.

(51) Int. Cl.
| | | |
|---|---|---|
| *A61K 31/4402* | (2006.01) |
| *A61P 31/14* | (2006.01) |
| *A61J 1/06* | (2006.01) |
| *A61K 9/00* | (2006.01) |
| *A61K 31/137* | (2006.01) |

(52) U.S. Cl.
CPC ............. *A61K 31/4402* (2013.01); *A61J 1/06* (2013.01); *A61K 9/0078* (2013.01); *A61K 31/137* (2013.01); *A61P 31/14* (2018.01)

(58) Field of Classification Search
CPC .............. A61K 31/4402; A61K 9/0078; A61K 31/137; A61P 31/14; A61J 1/06
See application file for complete search history.

(56) References Cited

U.S. PATENT DOCUMENTS

| | | | | |
|---|---|---|---|---|
| 6,702,997 B2 * | 3/2004 | Chaudry | ............. | A61K 9/0078 128/200.14 |
| 10,874,650 B1 * | 12/2020 | Ferrer | ................... | A61K 9/0043 |
| 2006/0073173 A1 * | 4/2006 | Banach | ................... | A61P 11/02 424/400 |
| 2006/0216353 A1 * | 9/2006 | Liversidge | ........... | A61K 9/0075 514/217.05 |

* cited by examiner

*Primary Examiner* — James D. Anderson
*Assistant Examiner* — William Y Lee
(74) *Attorney, Agent, or Firm* — Albert Bordas, P.A.

(57) ABSTRACT

Compositions for treatment or prevention of viral infections, such as influenza A and B, coronaviruses, including but not limited to COVID-19 and any variant thereof, and rhinoviruses, along with related treatment methods. Certain compositions according to preferred embodiments may comprise chlorpheniramine and albuterol administered by inhalation in nebulized form.

2 Claims, No Drawings

ANTIVIRAL AND VIRUCIDAL LUNG NEBULIZER COMPOSITIONS AND RELATED TREATMENT METHODS

BACKGROUND OF THE INVENTION

1. Field of the Invention

The present invention relates to antiviral and virucidal compositions, and more particularly, to antiviral and virucidal compositions administered by inhalation for the treatment of viral infections such as colds, influenza A and B, coronaviruses, and rhinoviruses, and other airways diseases and disorders in humans and animals.

2. Other Related Applications

The present application is a continuation/divisional of pending U.S. patent application Ser. No. 17/230,321 filed on Apr. 14, 2021, which is hereby incorporated by reference.

3. Description of the Related Art

Chlorpheniramine shows a potent inhibitory activity against divergent influenza A strains and influenza B strain and it protects mice from fatal challenge of avian H7N9 influenza virus. Chlorpheniramine also has been shown to inhibit influenza virus infections by targeting the early stage of virus life cycle, viral entry into the host cells. Chlorpheniramine has also been demonstrated to be superior to Oseltamivir (Tamiflu) in treating Influenza A/B.

Chlorpheniramine when given by inhalation produces significant bronchodilation. Studies demonstrate that Chlorpheniramine causes bronchodilation during resting period by acting on the circulating or tissue histamine in asthmatics, which contributes to an increase in resting bronchomotor tone.

Applicant believes that one of the closest references corresponds to applicant's own U.S. Pat. No. 10,874,650 issued on Dec. 29, 2020 for Antiviral and virucidal nasal spray compositions and related treatment methods. However, it differs from the present invention because Ferrer teaches compositions for treatment or prevention of viral infections, such as influenza A and B, coronaviruses, including but not limited to COVID-19, and rhinoviruses, along with related treatment methods. Certain compositions according to preferred embodiments of the invention may comprise chlorpheniramine, xylitol, and other inactive ingredients, such as aloe Vera and/or grapefruit seed extract.

SUMMARY OF THE INVENTION

The present invention is referred to a sterile nebulizer composition, which comprises antiviral/anti-infective Chlorpheniramine combined with albuterol, or budesonide, or xylitol, or ipratropium bromide in about 2 ml or less of saline solution for treatment of viral infections and other airways diseases and disorders in humans and animals.

The compositions may be used to treat various conditions, particularly conditions caused by viruses, including, for example, colds, influenza A and B, coronaviruses, including but not limited to COVID-19, rhinoviruses, and the like and/or may otherwise provide an antiviral effect, virucidal effect, and/or be preventative of viral disease. Some compositions and treatment methods disclosed herein may also be used to treat allergy symptoms, such as nasal drip, coughing, sneezing, sinusitis, and the like. The compositions may be used to treat airways diseases and disorders in humans and animals.

The compositions may further comprise a pharmaceutically-acceptable carrier such as aqueous saline solution carriers and water. A solution, which contain sodium chloride as the salt. Minor amounts of other ingredients such as pH adjusters (e.g., bicarbonate), emulsifiers or dispersing agents, buffering agents, preservatives, wetting agents and gelling agents may also be present.

In a more particular example of a treatment method according to some implementations, the method may comprise treating a viral infection, such as influenza A and B, coronaviruses, including but not limited to COVID-19 and any variant thereof, rhinoviruses, and any other viruses obtaining a composition for nebulization comprising chlorpheniramine maleate, referred to herein as chlorpheniramine, in some embodiments and implementations including other ingredients, such as albuterol.

In embodiments in which the antihistamine comprises chlorpheniramine, the chlorpheniramine may be present in the composition in a concentration of between about 0.01% and about 10% by mass, in more preferred compositions, between about 0.06 and about 4.0% by mass.

The features, structures, steps, or characteristics disclosed herein in connection with one embodiment or implementation may be combined in any suitable manner in one or more alternative embodiments or implementations. It should also be understood that any reference to a detail associated with an "embodiment" may be incorporated into and/or used with an "implementation," and vice versa.

The present invention is an antiviral and virucidal lung nebulizer composition comprising chlorpheniramine maleate in a concentration between about 0.01% and about 10% by mass in combination with a compound selected from the group consisting of fluticasone, budesonide, xylitol, albuterol, and ipratropium bromide; wherein the composition is suitable for administration by inhalation. In a preferred embodiment, the chlorpheniramine maleate is in a concentration between about 0.06% to about 4% by mass.

The antiviral and virucidal lung nebulizer composition may comprises chlorpheniramine maleate in a concentration between about 0.06% and about 4% by mass and albuterol in a concentration between about 0.08% and about 1% by mass. The chlorpheniramine maleate comprises a particle size less than about 5 microns.

The antiviral and virucidal lung nebulizer composition is used for treatment of viral infections and airways diseases and disorders in humans and animals. The viral infections are selected from the group consisting of colds, influenza A and B, coronaviruses specially COVID-19 and any variant thereof, and rhinoviruses. The composition is administered in nebulized form.

A method of treating viral infections in a subject in need of such treatment comprising administering by inhalation to the subject an antiviral and virucidal composition comprising chlorpheniramine maleate in a concentration between about 0.01% and about 10% by mass in combination with a compound selected from the group consisting of fluticasone, budesonide, xylitol, albuterol, and ipratropium bromide. Present invention may comprise any D-xylose (Erythritol, sorbitol, and maltitol). The chlorpheniramine maleate may be in a concentration between 0.06% and 4% by mass.

The method in that the antiviral and virucidal composition comprises chlorpheniramine maleate in a concentration between about 0.06% and about 4% by mass, and albuterol in a concentration between about 0.08% and about 1% by mass. The chlorpheniramine maleate and albuterol are dissolved together in a liquid carrier. The chlorpheniramine maleate and albuterol are dissolved in between about 1 ml and 2 ml of saline solution.

The method is used in the treatment of viral infections and airways diseases and disorders in humans and animals. The viral infections are selected from the group consisting of colds, influenza A and B, coronaviruses, and rhinoviruses, specifically COVID-19 and any new variants. The chlorpheniramine maleate comprises a particle size less than about 5 microns to allow nebulization and deposition in the lugs.

The method comprises administering a dose of chlorpheniramine maleate between about 4 to 12 mg and albuterol between about 80 mcg to 150 mcg every 6 to 8 hours.

A method of treating viral infections in a subject in need of such treatment comprising administering by inhalation to the subject a nebulized content of an ampoule having a liquid pharmaceutical composition comprising chlorpheniramine maleate in a concentration between about 0.06% and about 4% by mass in combination with a compound selected from the group consisting of fluticasone, budesonide, xylitol, albuterol, and ipratropium bromide, and a pharmaceutically acceptable carrier.

The method wherein the liquid pharmaceutical composition comprises chlorpheniramine maleate in a concentration between about 0.06% and about 4% by mass, albuterol in a concentration between about 0.08% and about 1% by mass, and a pharmaceutically acceptable carrier.

The ampoule comprises between about 0.5 ml to 5 ml of the liquid pharmaceutical composition. The liquid pharmaceutical composition has a pH in the range between about 3.5 and 7.5.

The method is used for treatment of viral infections and airways diseases and disorders in humans and animals. The viral infections are selected from the group consisting of colds, influenza A and B, coronaviruses, and rhinoviruses. In a preferred embodiment the viral infection is COVID-19 and any variant thereof.

The method comprises administering a dose of chlorpheniramine maleate between about 4 to 12 mg and a dose of albuterol between about 80 mcg to 150 mcg every 6 to 8 hours.

It is therefore one of the main objects of the present invention to provide an antiviral and virucidal lung nebulizer composition and related treatment methods.

It is another object of this invention to provide an antiviral and virucidal lung nebulizer composition and related treatment methods, which comprise chlorpheniramine maleate and albuterol administered by inhalation.

It is another object of this invention to provide an antiviral and virucidal lung nebulizer composition for the treatment of viral infection such as colds, influenza A and B, coronaviruses specifically COVID-19 and any variant thereof, and rhinoviruses.

It is another object of this invention to provide an antiviral and virucidal lung nebulizer composition for the treatment of airways diseases and disorders in humans and animals.

It is another object of this invention to provide an antiviral and virucidal lung nebulizer composition, which is effective against COVID-19.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The present invention is referred to antiviral and virucidal nebulized compositions and related treatment methods. Disclosed herein are various compositions that may be provided in a solution for inhalation by nebulization. Preferred embodiments of such compositions, and preferred implementations of related methods, may be used to treat and/or prevent various conditions caused by viruses, including colds, influenza, coronaviruses specifically COVID-19 and any variant thereof, rhinoviruses, or other viral infections. The compositions may be used for the treatment of airways diseases and disorders in humans and animals. However, it is anticipated that alternative embodiments and implementations may be made into suspensions, lozenges, tablets, capsules, topical compositions, and/or ingestible products, such as teas or other beverages.

As demonstrated by the working example below (Example 1), the present inventor has demonstrated that in vitro chlorpheniramine is highly effective against COVID-19. The composition tested eliminated more than 80% of the viral load in a virucidal assay that tested COVID-19 from the United States and Wuhan China.

In addition, to treating or prevent viral infections, the preferred compositions and treatment methods disclosed herein may combine the most desirable agents and concentrations into a single composition, preferably administered by inhalation, and may include other ingredients for decreasing various side effects.

In most preferred compositions and related treatment methods, an antihistamine is provided, such as, in preferred embodiments, chlorpheniramine. The chlorpheniramine may be present in the composition in a concentration between about 0.01 and about 10% by mass, more preferably, between about 0.06 and about 4% by mass.

Some compositions may include other ingredients, such as grapefruit see extract, benzalkonium chloride, and/or glycerine, preferably along with purified water. Thus, in some such embodiments, grapefruit seed extract may be included in the formulation in an amount between about 0.01 and about 3% by mass. Glycerine, if included, preferably ranges between about 0.05 and about 3% by mass. In embodiments comprising benzalkonium chloride, which may be a suitable substitute for grapefruit seed extract, may be present in a concentration of between about 0.05 and about 0.2% by mass. The remainder of the formulation may comprise (preferably purified) water. In some formulations, purified water may be present in a range from about 80 to about 98% by mass. In some such formulations, the purified water may be present in a range from about 80 to about 90% by mass. In a more preferred formulation, water may be present in a concentration of about 87.5%.

Additional more specific and more preferred embodiments of the invention are disclosed below. Although these compositions have very specific ingredients and concentrations, it should be understood that the concentrations of the ingredients in these compositions vary by around 5% from the concentrations provided herein.

The present invention provides an antiviral and virucidal lung nebulizer composition comprising chlorpheniramine maleate in a concentration between about 0.01% and about 10% by mass in combination with a compound selected from the group consisting of fluticasone, budesonide, xylitol, albuterol, and ipratropium bromide. The composition is suitable for administration by inhalation. In a preferred embodiment, the chlorpheniramine maleate is in a concentration between about 0.06% to about 4% by mass.

In a preferred embodiment, the antiviral and virucidal lung nebulizer composition comprises:

A) chlorpheniramine maleate in a concentration between about 0.06% and about 4% by mass; and B) albuterol in a concentration between about 0.08% and about 1% by mass.

The chlorpheniramine maleate and the albuterol in combination exhibit synergy. The chlorpheniramine maleate comprises a particle size less than about 5 microns.

The antiviral and virucidal lung nebulizer composition is used for treatment of viral infections and airways diseases and disorders in humans and animals. The viral infections are selected from the group consisting of colds, influenza A and B, coronaviruses specially COVID-19 and any variant thereof, and rhinoviruses. The composition is administered in nebulized form.

The present invention also provides a treatment method for treating viral infections comprising administering by inhalation to a subject an antiviral and virucidal composition comprising chlorpheniramine maleate in a concentration between about 0.01% and about 10% by mass in combination with a compound selected from the group consisting of fluticasone, budesonide, xylitol, albuterol, and ipratropium bromide. The chlorpheniramine maleate may be in a concentration between 0.06% and 4% by mass.

In a preferred embodiment, the treatment method comprises the antiviral and virucidal composition comprising:

A) chlorpheniramine maleate in a concentration between about 0.06% and about 4% by mass; and B) albuterol in a concentration between about 0.08% and about 1% by mass.

The chlorpheniramine maleate and albuterol are dissolved in a liquid carrier. The chlorpheniramine maleate and albuterol are dissolved in between about 1 ml and 2 ml of saline solution.

The method is used for treatment of viral infections and airways diseases and disorders in humans and animals. The viral infections are selected from the group consisting of colds, influenza A and B, coronaviruses, and rhinoviruses. In a preferred embodiment, the treatment method is used for the treatment of COVID-19 and any variant thereof. The chlorpheniramine maleate comprises a particle size less than about 5 microns. In a preferred embodiment, the method comprises administering a dose of chlorpheniramine maleate between about 4 to 12 mg and albuterol between about 80 mcg to 150 mcg every 6 to 8 hours.

In a preferred embodiment, the method of treating viral infections in a subject in need of such treatment comprises administering by inhalation to the subject a nebulized content of an ampoule having a liquid pharmaceutical composition comprising chlorpheniramine maleate in a concentration between about 0.06% and about 4% by mass in combination with a compound selected from the group consisting of fluticasone, budesonide, xylitol, albuterol, and ipratropium bromide, and a pharmaceutically acceptable carrier.

In a preferred embodiment, the liquid pharmaceutical composition comprises:

A) chlorpheniramine maleate in a concentration between about 0.06% and about 4% by mass;

B) albuterol in a concentration between about 0.08% and about 1% by mass; and

C) a pharmaceutically acceptable carrier.

The ampoule comprises between about 0.5 ml to 5 ml of the liquid pharmaceutical composition. The liquid pharmaceutical composition has a pH in the range between about 3.5 and 7.5.

The method is used for treatment of viral infections and airways diseases and disorders in humans and animals. The viral infections are selected from the group consisting of colds, influenza A and B, coronaviruses, and rhinoviruses. In a preferred embodiment the viral infection is COVID-19 and any variant thereof.

The method comprises administering a dose of chlorpheniramine maleate between about 4 to 12 mg and albuterol between about 80 mcg to 150 mcg every 6 to 8 hours.

The pharmaceutical composition of the present invention is used with a nebulizer or Metered Dose Inhaler (MDI). In a preferred embodiment, the ampoule contain between 1.5 and 3 ml of a sterile composition of Chlorpheniramine alone or in combination with, fluticasone, or budesonide, and/or Xylitol, and/or Albuterol, and/or Ipratropium bromide in a pharmaceutically acceptable carrier.

The ampoules contain between 0.5 to 5 ml of composition. The composition should be in a pharmaceutically acceptable carrier and buffered for human use to a pH of about 3.5-6.5.

The compositions of the present invention are free of preservative. The carrier is water for used for injection. In small proportion both inorganic and organic tonicity adjusting agents, excipients, and/or preservatives such as surfactants, stabilizers or other additives. Compounds like ethylenediaminetetraacetic acid (EDTA) or disodium salt, citric acid, nitrilotriacetic acid, benzalkonium chloride or benzoic acid may also be used.

All viral infections that evolve into pneumonia, especially Influenza and COVID-19, result from uncontrolled inflammation triggered in the bronchi and from there to the lung tissue. Several in-vitro and animal studies have demonstrated the anti-inflammatory effect of chlorpheniramine maleate and albuterol.

In another preferred embodiment, the composition comprises chlorpheniramine at a dose 0.5 mg to 12 mg administered by inhalation every six, eight or twelve hours with a maximum dose of 24 mg a day. Chlorpheniramine may be alone or in combination with:

A) Fluticasone 50 mcg to 250 mcg, administered every 12 hours;

B) Budesonide from 80 mcg to 4 mg, administered every 12 hours;

C) Xylitol between 2% and 20%, administered every 6-8 hours;

D) Albuterol from 0.080% to 1%—a dose between about 0.60 mg to 3 mg, administered every 6-8 hours;

E) Ipratropium bromide from 0.01 to 1%—a dose between about 15 mcg to 1 mg, administered every 6-8 hours.

In addition, the combination of albuterol and chlorpheniramine potentiate each other anti-inflammatory effect. The bronchodilator effect of Albuterol will allow chlorpheniramine to penetrate the deepest part of the lung tissue, thus blocking the virus and the inflammatory response.

For nasal delivery, the inventor performed tests that show that the spray pump generates particle size >10 microns more than 90% of the spray content.

In a more preferred embodiment, the present invention comprises chlorpheniramine maleate comprising a particle size less than 5 microns to be delivered by nebulization.

Example 1

In a first working example of a study testing the efficacy of certain compositions disclosed herein, a composition was obtained comprising chlorpheniramine maleate at 3.6 mg/mL or 0.4% concentration. The composition further comprised xylitol at a concentration of about 11% by mass, glycerin, GSE of 0.2%, sodium bicarbonate, and purified water.

A viral stock of SARS-CoV-2, USA-WA1/2020 strain, was prepared before testing through growth in Vero 76 cells. The culture medium for the prepared stock (test medium) was MEM with 2% fetal bovine serum and 50 µg/mL gentamicin.

The composition was mixed directly with virus solution at a proportion of about 90% compound preparation and 10% virus solution. A single concentration was tested in triplicate. Test medium without virus was added to one tube of the prepared composition to serve as a toxicity control. Ethanol (70%) was tested in parallel as a positive control, and water only was tested as a virus control. The solution and virus were incubated at room temperature (22+/−2° C.) for 25 minutes. The solution was then neutralized through 1/10 dilution in a test medium.

Surviving virus from each sample was then quantified with standard end-point dilution assays. More particularly, samples were serially diluted 1/10 in the test medium. Then, 100 µgL of each dilution was plated into quadruplicate wells of 96-well plates containing 80-90% confluent Vero 76 cells. The plates were then incubated at 37+/−2° C. under 5% $CO_2$ for six days. Each well was then scored for the presence or absence of virus. The end-point titer (CCID50) values were calculated with the Reed-Muench (1948) equation, with which those of ordinary skill in the art are familiar. A statistical analysis was then performed. In particular, three independent replicates of each sample were tested, and the average and standard deviation were calculated. Results were compared with untreated controls by one-way ANOVA with Dunnett's multiple comparison test in GraphPad Prism (version 8) software.

Virus controls were tested in water, and the reduction of virus in the test wells compared with the virus control wells was calculated as the log reduction value (LRV). Toxicity controls were tested with medium not containing virus to determine whether the samples were toxic to cells. Neutralization controls were tested to ensure that viral inactivation did not continue after the specified contact time and that any residual sample in the titer assay plates did not inhibit growth and detection of surviving virus.

This procedure was performed by adding toxicity samples to titer test plates and then spiking each well with a small amount of virus that would produce an observable cytopathogenic effect during the incubation period.

Table A, which is reproduced below, illustrates the virucidal efficacy of the composition used in the study of Example 1 against SARS-CoV-2 after a 25-minute incubation with virus at 22+/−2° C. This table shows the viral titer and LRV values for SARS-CoV-2 after incubation with a single concentration of the nasal composition used in the study.

TABLE A

|  | Concentration | Incubation | Virus Titer | Log Reduction Value |
|---|---|---|---|---|
| Nasal Spray | 90% | 25 minutes | 1.7 ± 0.0 | 2.5*** |
| Ethanol | 67.5% | 25 minutes | 1.0 ± 0.6 | 3.2*** |
| Virus Control | N/A | 25 minutes | 4.2 ± 0.4 | N/A |

The Virus Titer in Table A was taken using Log 10 CCID50/mL which is defined as 50% cell culture infectious dose per mL of the virus per 0.1 mL and is the average of three replicates±standard deviation. Similarly, the Log Reduction Value in Table A is the reduction of virus compared with that of the virus control ***P<0.001 by one-way ANOVA and Dunnett's post-test, compared with untreated virus control (water). For wells with undetectable virus a value equal to the lower limit of detection was assigned for statistical analyses.

The results of the study of Example 1 demonstrate that toxicity was observed in the top dilution (1/10). Virus was observed below that dilution and therefore did not affect calculations of viral titer or LRV. After a 25-minute contact time, the nasal spray reduced the levels of virus from 4.2 to 1.7 log 10 CCID50 per 0.1 mL, a statistically significant reduction of 2.5 log 10 CCID50. Neutralization controls demonstrated that the residual sample did not inhibit viral growth and detection in the endpoint titer assays. Virus controls and positive controls performed as expected in the study.

This working example demonstrates the strong virucidal effect against SARS-CoV-2 of a composition containing chlorpheniramine. The present inventor believes that combining the tested solution with albuterol, and/or ipratropium bromide, and/or fluticasone propionate, and/or budesonide may further enhance efficacy.

Example 2

In another more particular example of a composition and/or related treatment method for treating or preventing viral infections, the composition is administered preferably by inhalation in the form of a nebulized composition; the composition may comprise the following ingredients in at least approximately the concentrations (by mass) presented in the chart below. However, as mentioned above, these concentrations may vary by 5% in certain alternative embodiments and related methods. Similarly, one or more of these ingredients may be omitted and/or replaced with an alternative substantially similar ingredient available to those of ordinary skill in the art in still other embodiments and related methods.

| Chlorpheniramine | 0.06% to 4% |
|---|---|
| albuterol | 0.080% to 1% |
| Purified Water | 80% to 90% |

Example 3

In another more particular example of a composition, preferably administered by inhalation in form of a nebulized composition, and/or related treatment method for treating or preventing viral infections, the composition may comprise the following ingredients in at least approximately the concentrations (by mass) presented in the chart below. However, as mentioned above, these concentrations may vary by 5% in certain alternative embodiments and related methods. Similarly, one or more of these ingredients may be omitted and/or replaced with an alternative substantially similar ingredient in still other embodiments and related methods.

| Chlorpheniramine | 0.01 to 10% |
|---|---|

-continued

| | |
|---|---|
| | (more preferably 0.4 to 1.0%) |
| Xylitol | 2 to 20% |
| Purified Water | 70 to 90% |

Example 4

In yet another even more particular example of a composition, preferably administered by inhalation in the form of a nebulized composition, and/or related treatment method for treating or preventing viral infections the composition may comprise the following ingredients in at least approximately the concentrations (by mass) presented in the chart below.

| | |
|---|---|
| Chlorpheniramine | 0.01% to 10% (in more particular compositions, 0.4%) |
| Fluticasone propionate | 0.006% to 0.08% |
| Purified Water | 80 to 90% |

Because this is a more potent composition than that of Example 2, in certain implementations of treatment methods involving this composition, the composition may be delivered to a subject by inhalation every 12 hours.

Example 5

In another example of a composition according to other embodiments, preferably administered by inhalation in the form of a nebulized composition, and/or related treatment method for treating or preventing viral infections, the composition may comprise the following ingredients in at least approximately the concentrations (by mass) presented in the chart below.

| | |
|---|---|
| Chlorpheniramine | 0.01 to 10.0% |
| Budesonide | 0.009 to 1.3% |
| Purified Water | 80 to 90% |

Because this is a more potent composition than that of Example 2, in certain implementations of treatment methods involving this composition, the composition may be delivered to a subject by inhalation every 12 hours.

Example 6

In still another example of a composition according to other embodiments, preferably administered in the form of a nebulized composition, and/or related treatment method for treating or preventing viral infections, the composition may comprise the following ingredients in at least approximately the concentrations (by mass) presented in the chart below.

| | |
|---|---|
| Chlorpheniramine | 0.01 to 10.0% |
| Ipratropium bromide | 0.01 to 1% |
| Purified Water | 80 to 90% |

It will be understood by those having skill in the art that changes may be made to the details of the above-described embodiments without departing from the underlying principles presented herein. For example, the compositions disclosed herein may be administered orally, via a mister or atomizer, nebulization, liquid drops from a dropper, topically (in some cases using a cotton swab or the like), and/or via any other suitable manner of administration. In addition, alternative compositions and treatment methods are contemplated in which the compositions may be in form of suspensions, lozenges, tablets, capsules, topical compositions, and/or ingestible products, such as teas or other beverages, for example. In addition, any suitable combination of various embodiments, or the features thereof, is contemplated.

Any methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element.

REFERENCES

G. Ferrer, J. Westover, "*In Vitro Virucidal Effect of Intranasally Delivered Chlorpheniramine Maleate Compound Against Severe Acute Respiratory Syndrome Coronavirus* 2 (*SARS-CoV*-2)", Utah State University, Institute for Antiviral Research and Ferrer Medical Innovations Nova Southeastern University, May 2020.

O'Byrne, et al. "*The Protective Effect of Inhaled Chlorpheniramine and Atropine on Bronchoconstriction Stimulated by Airway Cooling" American review of respiratory disease,* 1983, 128(4), 611-617.

Jagdeep Chugh, et al. "*The Effect of Aerosolized Chlorpheniramine Maleate on Exercise Induced Bronchospasm and Gas Exchange in Asthmatics", Journal of The Association of Physicians of India*, Vol. 68, April 2020.

Doyle W J, McBride T P, Skoner D P, Maddern B R, Gwaltney J M Jr, Uhrin M. "*A double-blind, placebo-controlled clinical trial of the effect of chlorpheniramine on the response of the nasal airway, middle ear and eustachian tube to provocative rhinovirus challenge", Pediatr Infect Dis J.* 1988 March, 7(3): 229-38.

Van Toor B S, Buchwald A, Stengele E, Trenk D, Gercek C, de Mey C M. "*Systemic bioavailability of nasally applied chlorphenamine maleate (0.4% nasal spray) relative to tablets administered perorally*". Int J Clin Pharmacol Ther. 2001 April, 39(4): 173-8.

Aydin, "*Could Antihistamines Help in the Treatment and Spread of COVID-19 Via Re-Modulating Cytokines and by Reducing Sneezing?*" Acta Scientific Nutritional Health 4.4 (2020) 172-173. https://actascientific.com/ASNH/ASNH-04-0684.php.

H. W. Chang, et al., "*A common signaling pathway leading to degranulation in mast cells and its regulation by CCR1-ligand, Allergy*", Eur. J. Allergy Clin. Immunol. 75 (2020) 1371-1381, https://doi.org/10.1111/all.14186.

Gwaltney J M Jr, Winther B, Patrie J T, Hendley J O., "*Combined antiviral-antimediator treatment for the common cold.*" J Infect Dis. 2002 Jul. 15; 186 (2):147-54.

P. Conti, et al., "*Mast cells activated by SARS-CoV-2 release histamine, which increases IL-1 levels causing cytokine storm and inflammatory reaction in COVID-19*"— PubMed (nih.gov).

Li X, Zhang C, Liu L, Gu M. "*Existing bitter medicines for fighting 2019-nCoV-associated infectious diseases*", FASEB J. 2020 May; 34(5):6008-6016.

Haiping Zhang, et al. "*Deep Learning Based Drug Screening for Novel Coronavirus 2019—nCov COVID*"

Graham A C, et. al, "*Mast cells and influenza A virus: Association with allergic responses and beyond*". Front Immunol. 2015; 6: 1-12.

Kilinc E, Baranoglu Y. "*Mast cell stabilizers as a supportive therapy can contribute to alleviate fatal inflammatory responses and severity of pulmonary complications in COVID-19 infection*" Anadolu Klin Tip Bilim Derg. 2020; 25 (Supplement 1): 111-8

He L, et al. "*Expression of elevated levels of pro-inflammatory cytokines in SARS-CoV-infected ACE2+ cells in SARS patients: relation to the acute lung injury and pathogenesis of SARS*" J Pathol. 2006 November; 210 (3):288-97.

Russell B, et al. "*Associations between immune-suppressive and stimulating drugs and novel COVID-19—a systematic review of current evidence*", 2020; 14:1022.

Wang J, et al. "*Advances in the research of mechanism of pulmonary fibrosis induced by Corona Virus Disease 2019 and the corresponding therapeutic measures*", Zhonghua Shao Shang Za Zhi. 2020; 36:6.

Ramos L, et al. "*Mast Cell Stabilization Improves Survival by Preventing Apoptosis in Sepsis. J Immunol.* 2010; 185(1): 709-16.

Hu Y, et al. Mast. "*Cell-Induced Lung Injury in Mice Infected with H5N1 Influenza Virus*", J Virol. 2012; 86(6): 3347-56.

Lee J, Van Hecke O, Roberts N. "*Vitamin D: A rapid review of the evidence for treatment or prevention in COVID-19*". The Centre for Evidence-*Based Medicine, University of Oxford.* 2020 [cited 2020 May 16]. Available from: https://www.cebm.net/covid-19/vitamin-d-a-rapid-review-of-the-evidence-for-treatment-or-prevention-in-covid-19/COVID.

Gitahy Falcao Faria C, et al. "*Antihistamine and cationic amphiphilic drugs, old molecules as new tools against the COVID-19*", Med Hypotheses. 2021 Jan. 24; 148:110508.

Reznikov L R, et al. "*Identification of antiviral antihistamines for COVID-19 repurposing*", Biochem Biophys Res Commun. 2020, December; 3: 50006-291X(20) 32140-9.

Eldanasory O A, et al. "*Histamine release theory and roles of antihistamine in the treatment of cytokines storm of COVID-19*", Travel Med Infect Dis. 2020 Sep.-Oct.; 37:101874.

Ennis M, Tiligada K. "*Histamine receptors and COVID-19*", Inflamm Res. 2021 January; 70(1): 67-75.

Ge S, et al. "*Repositioning of histamine H1 receptor antagonist: Doxepin inhibits viropexis of SARS-CoV-2 Spike pseudovirus by blocking ACE2*", Eur J Pharmacol. 2021 Jan. 23; 896: 173897.

Morán Blanco J I, et al. "*Antihistamines and azithromycin as a treatment for COVID-19 on primary health care*" A retrospective observational study in elderly patients. Pulm Pharmacol Ther. 2021 Jan. 16; 67:101989.

Westover J B, Ferrer G, Vazquez H, Bethencourt-Mirabal A, Go C C. "*In Vitro Virucidal Effect of Intranasally Delivered Chlorpheniramine Maleate Compound Against Severe Acute Respiratory Syndrome Coronavirus 2*" Cureus. 2020 Sep. 17; 12(9):e10501.

Go C C, Pandav K, Sanchez-Gonzalez M A, Ferrer G. "*Potential Role of Xylitol Plus Grapefruit Seed Extract Nasal Spray Solution in COVID-19: Case Series Cureus*" 2020 Nov. 3; 12(11):e11315.

Ferrer G., et al. *A Nasal Spray Solution of Grapefruit Seed Extract plus Xylitol Displays Virucidal Activity Against SARS-Cov-2 In Vitro.* https://doi.org/10.1101/2020.11.23.394114

Mark L Cannon, Jonna B. Westover, Reiner Bleher, Marcos A. Sanchez-Gonzalez, Gustavo A. Ferrer. "*In Vitro Analysis of the Anti-viral Potential of nasal spray constituents against SARS-CoV-2.* https://doi.org/10.1101/2020.12.02.408575

Go C C, Pandav K, Sanchez-Gonzalez M A, Ferrer G. Potential "*Role of Xylitol Plus Grapefruit Seed Extract Nasal Spray Solution in COVID-19: Case Series. Cureus.*", 2020; 12(11):e11315. Published 2020 Nov. 3.

Xu W, et al. "*The Antihistamine Drugs Carbinoxamine Maleate and Chlorpheniramine Maleate Exhibit Potent Antiviral Activity Against a Broad Spectrum of Influenza Viruses*", Front Microbiol. 2018 Nov. 6; 9:2643.

What is claimed is:

1. An antiviral and virucidal composition comprising chlorpheniramine maleate in a concentration between about 0.06% and 4% by mass in combination with albuterol in a concentration between about 0.08% and about 1% by mass, said chlorpheniramine maleate comprises a particle size less than about 5 microns, wherein the composition is suitable for administration by inhalation.

2. A nebulizer comprising the composition of claim 1.

\* \* \* \* \*